United States Patent [19]

Murray et al.

[11] Patent Number: 5,182,288
[45] Date of Patent: Jan. 26, 1993

[54] SUBSTITUTED N-BIPHENYLYL LACTAMS

[75] Inventors: William V. Murray, Belle Mead; Michael P. Wachter, Bloomsbury, both of N.J.

[73] Assignee: Ortho Pharmaceutical Corporation, Raritan, N.J.

[21] Appl. No.: 791,939

[22] Filed: Nov. 13, 1991

[51] Int. Cl.5 ................. C07D 211/40; C07D 227/087
[52] U.S. Cl. ..................................... 514/278; 514/326; 514/327; 546/16; 546/210; 546/221
[58] Field of Search ...................... 546/210, 16, 221; 514/278, 326, 327

Primary Examiner—C. Warren Ivy
Assistant Examiner—P. G. Spivack

[57] ABSTRACT

This invention relates to novel N-biphenylyl lactam compounds having a substituted methylidene or methyl moiety adjacent to the lactam nitrogen, and pharmaceutically acceptable salts thereof.

The compounds are angiotensin II receptor antagonists, and are useful in treating hypertension (lowering high blood pressure), congestive heart failure, elevated ocular pressure, cerebral stroke, angina, cardiac insufficiency, myocardial infarction or diabetic nephropathy.

The invention also relates to a pharmaceutical composition comprising a compound of the invention, a method of treating a physiological condition in a mammal that is mediated by angiotensin II which comprises administering to the mammal an effective amount of a compound of the invention, and novel processes for preparing the compounds of the invention.

10 Claims, No Drawings

SUBSTITUTED N-BIPHENYLYL LACTAMS

FIELD OF THE INVENTION

This invention relates to novel compounds of the following formula

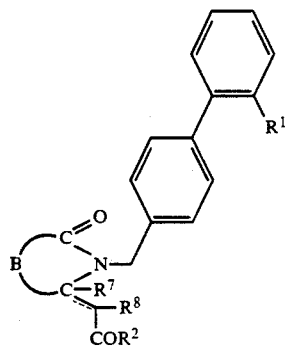

wherein B is a bisfused radical of the following formula

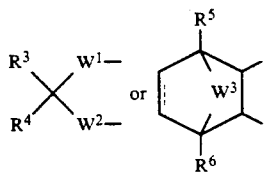

The invention also relates to a pharmaceutical composition comprising a compound of the invention, a method of treating a physiological condition in a mammal that is mediated by angiotensin II which comprises administering to the mammal an effective amount of the angiotensin II receptor antagonist which is a compound of the invention, and novel processes for preparing the compounds of the invention.

The compounds are angiotensin II receptor antagonists, and are useful in treating hypertension (lowering high blood pressure), congestive heart failure, elevated ocular pressure, cerebral stroke, angina, cardiac insufficiency, myocardial infarction or diabetic nephropathy.

BACKGROUND OF THE INVENTION

The renin-angiotensin system is one of the primary regulatory mechanisms for blood pressure in mammals. M. Ondetti et al., *Science*, 196, 441 (1977) and M. Ondetti et al., *J. Med. Chem.*, 24, 355 (1981) disclose captopril, as a noteworthy drug that acts on the renin-angiotensin system. A. Patchette et al., *Nature*, 288, 280 (1980) disclose enalapril, as another noteworthy drug that acts on the renin-angiotensin system. Both compounds and subsequent derivatives are ACE (angiotensin converting enzyme) inhibitors and are used as antihypertensive agents. Another site for inhibition of angiotensin is the angiotensin II receptor. European Patent Application No. 253,310A discloses a preferred compound of the following formula

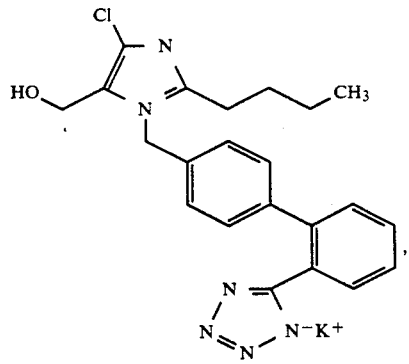

as an orally active angiotensin II receptor antagonist. European Patent Application No. 399,731A discloses a preferred compound of the following formula

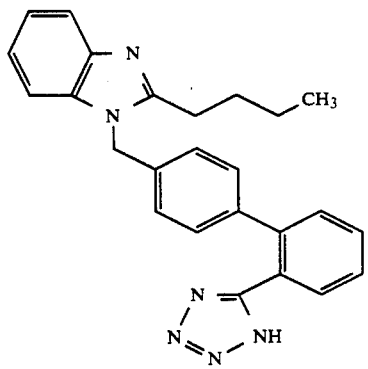

as an angiotensin II receptor antagonist. European Patent Application 412,848A discloses the compound of the following formula

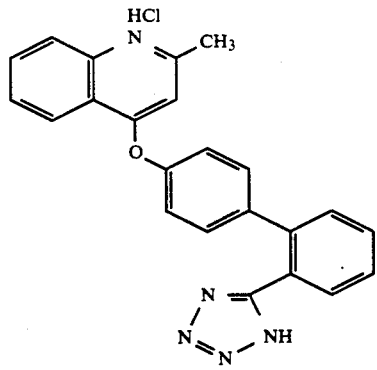

as an angiotensin II receptor antagonist.

The aforesaid references, however, do not disclose the N-biphenylyl lactams of the present invention.

DETAILED DESCRIPTION OF THE INVENTION

This invention relates to novel compounds of the following formula

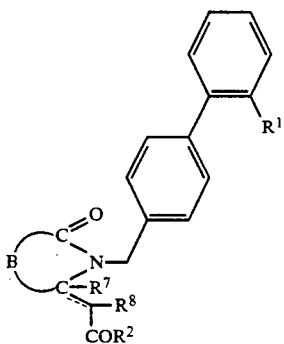

wherein B is a bisfused radical of the following formulae

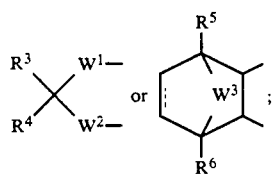

$W^1$ is $(CH_2)_m$;

m is 0, 1, 2, or 3;

$W^2$ is $(CH_2)_n$;

n is 0, 1, 2, or 3

$W^3$ is $(CH_2)_p$, $C=CG^1G^2$, O, S or NH;

p is 1, 2, 3, or 4;

$G^1$ and $G^2$ are independently selected from hydrogen, $C_{1-6}$ alkyl, phenyl or substituted phenyl;

$R^1$ is carboxyl, $C_{1-4}$ alkoxycarbonyl, (HO)HNCO, (HO)($C_{1-6}$ alkyl)NCO, ($C_{1-4}$ alkoxy)($C_{1-6}$ alkyl)NCO, cyano, tetrazolo, $SO_3H$, $PO(OH)_2$, $NHSO_2CR^9{}_3$ or $HNSO_2$aryl;

$R^2$ is hydroxy, $C_{1-4}$ alkoxy, ($C_{1-6}$ alkyl)HN, di($C_{1-6}$ alkyl)N, (HO)HN, (HO)($C_{1-6}$ alkyl)N, ($C_{1-4}$ alkoxy)($C_{1-6}$ alkyl)N, phenoxy or substituted phenoxy;

$R^3$ and $R^4$ are each independently hydrogen, $C_{1-6}$ alkyl, $C_{3-8}$ cycloalkyl, aryl, or $R^3$ and $R^4$ taken together form a $C_{3-8}$ carbocyclic ring;

$R^5$ and $R^6$ are each independently hydrogen, $C_{1-6}$ alkyl or $C_{1-4}$ alkoxy;

$R^7$ is hydrogen or hydroxy;

$R^8$ is hydrogen;

$R^7$ and $R^8$ taken together form a bond;

$R^9$ is $C_{1-6}$ alkyl or fluoro;

the ≡ bond is a single or a double bond; and pharmaceutically acceptable salts thereof; with the proviso that m and n are not both 0; and where $R^7$ and $R^8$ are hydrogen or when $R^7$ is hydroxy and $R^8$ is hydrogen then the ≡ bond is a single bond The invention also pertains to the species of the following formulae:

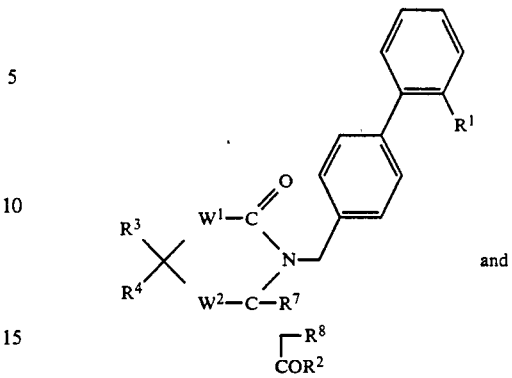

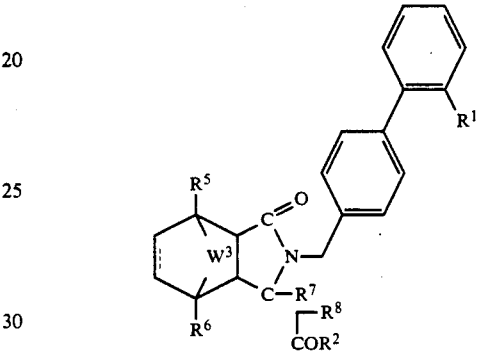

wherein $R^1$, $R^2$, $R^3$, $R^4$, $R^5$, $R^6$, $R^7$, $R^8$, $W^1$, $W^2$, $W^3$ and the ≡ bond are as defined above.

An embodiment of the invention pertains to the compounds wherein $W^3$ is $(CH_2)_p$ or O. Another embodiment of the invention pertains to the compounds wherein $W^1$ is $(CH_2)_p$, $W^2$ is $(CH_2)_p$ and $R_2$ and $R_4$ are lower alkyl. Another embodiment of the invention pertains to the compounds wherein $R^1$ is carboxyl, cyano, $C_{1-4}$ alkoxycarbonyl or tetrazolo, and more preferably tetrazolo. Yet, another embodiment of the invention pertains to the compounds wherein $R^2$ is hydroxy, $C_{1-4}$ alkoxy, phenoxy or substituted phenoxy. A preferred embodiment of the invention pertains to compounds wherein $R^7$ and $R^8$ taken together form a bond.

Preferred species of the invention are selected from the group consisting of: 3-carbethoxymethyliden-2-[4-(2-tetrazolophenyl)benzyl]-4,7-endoethylene-1,3,4,7-tetrahydro-1-oxoisoindole; 3-carbethoxymethyliden-2-[4-(2-cyanophenyl)benzyl]-4,7-endoethylen-1,3,4,7-tetrahydro-1-oxoisoindole; 3-carbethoxymethyliden-2-[4-(2-tetrazolophenyl)benzyl]-4,7-endopropyl-1,3,4,7-tetrahydro-1-oxoisoindole pyridinium salt; 6-carbethoxymethyliden-4-spirocyclopentyl-1-[4-(2-tetrazolophenyl)benzyl]piperidin-2-one pyridinium salt; 3-carbomethoxymethyliden-2-[4-(2-tetrazolophenyl)benzyl]-4-methoxy-4,7-endoethylen-1,3,4,7-tetrahydro-1-oxoisoindole pyridinium salt; 3-carbethoxymethyliden-2-[4-(2-tetrazolophenyl)benzyl]-4,7-endomethylen-1,3,4,5,6,7-hexahydro-1-oxoisoindole; 3-carbethoxymethyliden-2-[4-(2-tetrazolophenyl)benzyl]-4,7-endoethylen-1,3,4,5,6,7-hexahydro-1-oxoisoindole pyridinium salt; 6-carbethoxymethyliden-4-ethyl-4-methyl-1-[4-(2-tetrazolophenyl)benzyl]piperdin-2-one pyridinium salt; and 6-carbethoxymethyliden-4,4-dimethyl-1-[4-(2-tetrazolophenyl)benzyl]piperdin-2-one pyridinium salt. Individually preferred species include 3-carbethoxymethyliden-2-[4-(2-tetrazolophenyl)benzyl]-4-methoxy-4,7-endoethylen-1,3,4,7-tetrahydro-1-oxoisoindole pyridinium salt; 3-carbethoxymethyliden-2-[4-(2-tetrazolophenyl)benzyl]-4,7-endomethylen-1,3,4,5,6,7-hexahydro-1-oxoisoindole; 3-carbethoxymethyliden-2-[4-(2-tetrazolophenyl)benzyl]-4,7-endoethylen-1,3,4,5,6,7-hexahydro-1-oxoisoindole pyridinium salt; 6-carbethoxymethyliden-4-spirocyclopentyl-1-[4-(2-tetrazolophenyl)benzyl]piperidin-2-one pyridinium salt; 6-carbethoxymethyliden-4-ethyl-4-methyl-1-[4-(2-tetrazolophenyl)benzyl]piperdin-2-one pyridinium salt; and 6-carbethoxymethylen-4-ethyl-6-hydroxy-4-methyl-1-[4-(2-tetrazolophenyl)benzyl]piperidin-2-one pyridinium salt.

The compounds of the invention also include their individual stereoisomers, i.e., E or Z, and mixtures thereof.

The alkyl portion of any of the substituent $R^1$, $R^2$, $R^3$, $R^4$, $R^5$, $R^6$, $G^1$ and $G^2$ includes $C_{1-6}$ straight- or branched-chain alkyl moieties, such as methyl, ethyl, propyl, isopropyl, butyl, tert-butyl or hexyl; the alkoxy portion of any of the substituents $R^1$, $R^2$, $R^5$ and $R^6$ includes $C_{1-4}$ straight- or branched-chain alkoxy moieties, such as methoxy, ethoxy, isopropoxy or butoxy; the $C_{3-8}$ cycloalkyl moiety includes cyclopropyl, methylcyclopropyl, cyclopentyl, methyl cyclopentyl or cyclohexyl; the $C_{3-8}$ carbocyclic includes cyclopropyl, cyclopentyl, cyclohexyl, cycloheptyl or methylcyclohexyl; and the substituent on the substituted phenyl or phenoxy moiety includes halo, such as chloro, bromo or fluoro, cyano, nitro, hydroxy, $C_{1-6}$ alkyl as defined supra, and $C_{1-4}$ alkoxy as defined supra.

The invention also relates to a novel process for preparing compounds of the invention as disclosed in Scheme I.

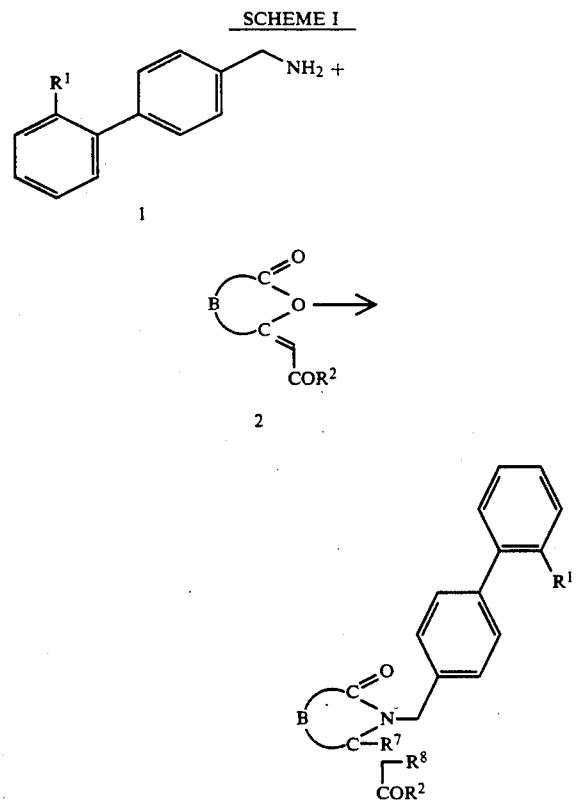

SCHEME I

The process comprises the step of condensing the biphenylylmethylamine (1), wherein $R^1$ is carboxyl, $C_{1-4}$ alkoxycarbonyl, (HO)HNCO, (HO)($C_{1-6}$ alkyl)NCO, ($C_{1-4}$ alkoxy)($C_{1-6}$ alkyl)NCO, cyano, tetrazolo, $SO_3H$, $PO(OH)_2$, $NHSO_2CR^9_3$ or $NHSO_2$aryl, with an appropriate cyclic enol-lactone (2) wherein B and $R^2$ are as defined above. In particular, the condensation of 1 and 2 is carried out in a solvent such as toluene, xylene or pyridine, to yield 3 wherein $R^7$ and $R^8$ taken together form a bond by heating at about 70° to 138° C. for about 1 to 24 hours, and to yield 3 wherein $R^7$ is hydroxy, and $R^8$ is hydrogen by heating at 20° to 50° C. for about 1 to 12 hours. The products are isolated by removing the solvent in vacuo and the residue is chromatographed on silica gel, using an appropriate solvent mixture, e.g., hexane/ethyl acetate, as the mobile phase to yield compound (3) as oils or solids. Alternatively, compound 3, wherein $R^7$ and $R^8$ form a bond, can be formed by the treatment of compound 3, wherein $R^7$ is hydroxy and $R^8$ is hydrogen, by heating in the presence of a solvent such as toluene or xylene at a temperature of about 100°–140° C.

The method for preparing 2 is essentially described as by M. Kayser et al., *Can. J. Chem.*, 67(9), 1401 (1989); I. Doyle et al., *Aust. J. Chem.*, 35, 1903 (1982); M. Janda et al., *Coll. Czech. Chem. Comm.*, 48, 96 (1983) and W. Wadsworth, In Organic Reactions, 25, 73 (1977) W. Dauben, ed.

Compound (1), wherein $R^1$ is carboxyl, $C_{1-4}$ alkoxycarbonyl, cyano, tetrazolo or nitro, is prepared as essentially described in European Patent Application No. 412,594.

Compound 3 wherein $R^1$ is nitro, is prepared by condensation of compound 1 where $R^1$ is nitro with 2 as above. The case where $R^1$ is an amine is prepared by reducing 3 where $R^1$ is nitro by dissolving it in a solvent such as THF or ethyl acetate, and then adding an appropriate catalyst such as Pd or Pt. The mixture is agitated under $H_2$ in a pressure reactor (Parr hydrogenator) (about 20 to 60 psi) at about 10° to 40° C. for about 1 to 25 hours. The catalyst is removed by filtration and the solvent is removed in vacuo to yield the corresponding amine. In the alternative, the reduction is carried out in situ by dissolving 3 where $R_1$ is nitro in an appropriate solvent, e.g., an alcohol such as ethanol or methanol, and then adding an appropriate catalyst such as Pd or Pt. The mixture is heated at about 40° C. to reflux for about 1 to 16 hours. The catalyst is removed by filtration, and the solvent is removed in vacuo to yield the corresponding amine. Compound 3 where $R^1$ is $NHSO_2CR^9_3$ or $NHSO_2$aryl is prepared by treating the corresponding amine with a sulfonating agent of the formula $XSO_2CR^9_3$ or $XSO_2$aryl wherein $R^9$ is as defined above, and X is a leaving group such as chloro or bromo, in a solvent such as methylene chloride or THF, at about 0° to 40° C. for about 1 to 24 hours to yield the corresponding sulfonamide.

Compound (1), wherein $R^1$ is (HO)HNCO, (HO)($C_{1-6}$ alkyl) NCO or ($C_{1-4}$ alkoxy)($C_{1-6}$ alkyl)NCO, is prepared by: (1) converting 1-(4-methylphenyl)benzoic acid to an appropriate hydroxamic acid as essentially described by W. Murray et al., in *Synthesis*, (1), 18 (1991); (2) protecting the formed hydroxamic acid with a silyl protecting agent as essentially described by L. Birkofer et. al., *Ang. Chem. Int. Ed.*, 4, 417 (1965); (3) converting the silyl protected hydroxamic acid to the corresponding protected 2-(4-aminomethylphenyl)phenyl hydroxamic acid as essentially described in European Patent Application No. 412,594; and (4) deprotecting the silyl protected 2-(4-aminomethylphenyl)phenyl hydroxamic acid as essentially described by E. J. Corey et al., *J. Am. Chem. Soc.*, 94, 2549 (1972).

Compound (1), wherein $R^1$ is $SO_3H$ or $P(O)(OH)_2$, is prepared by reducing 2-(4-methylphenyl)nitrobenzene as above. The amine is also reacted according to the procedures of H. Meerwein et al., *Chem. Ber.*, 90, 841 (1957) to yield the corresponding sulfonic acid, and of G. Doak et al., *J. Amer. Chem. Soc.*, 73, 5658 (1951); 74, 753 (1952); 75, 683 (1953); *J. Org. Chem.*, 29, 2382 (1964); and 30, 660 (1965) to yield the corresponding phosphonic acid. The resultant sulphonic acid and phosphonic acid compounds are then converted to compound (1) as described in European Patent Application No. 412,594.

In the compounds of the invention, the reduction of the endocyclic double bond, the===bond in the bisfused radical, i.e., B, is carried out as described supra regarding the reduction of the nitro group. The product is isolated by filtration and concentration.

In the compounds of the invention, the reduction of the exocyclic double bond, the 3-methylidene bond, i.e., where $R^7$ and $R^8$ taken together form a bond is effected by dissolving a compound, having the exocyclic bond in an appropriate solvent, e.g., THF or ethyl acetate, and then adding an appropriate catalyst such as Pd/C or Pt (0.5–10 mol %). The mixture is agitated under $H_2$ (about 50 to 400 psi) at about 10° to 70° C. for about 1 to 48 hours. The catalyst is removed by filtration, and the solvent is removed in vacuo to yield the reduced compound.

The compounds are angiotensin II receptor antagonists, and are useful in treating hypertension (lowering high blood pressure), congestive heart failure, elevated ocular pressure, cerebral stroke, angina, cardiac insufficiency, myocardial infarction and/or diabetic nephropathy.

Pharmaceutical compositions comprising a compound of the invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed. For example, in the case of oral liquid preparations (such as suspensions, elixirs and solution), water, glycols, oils, alcohols, flavoring agents, preservatives, coloring agents and the like may be used. In the case of oral solid preparations (such as, for example, powders, capsules and tablets), carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally be in the form of a dosage unit, e.g., tablet, capsule, powder, injection, teaspoonful and the like, containing from 0.1 to about 1000 mg/kg, and preferably from about 1 to 200 mg/kg of the active ingredients.

The following experimental examples describe the invention in greater particularity and are intended to be a way of illustrating but not limiting the invention.

EXAMPLES

Melting points were determined on a Thomas-Hoover apparatus and are uncorrected. The infrared spectra (IR) were recorded on a Beckman Instruments IR-B spectrophotometer and are expressed in reciprocal centimeters. Nuclear magnetic resonance (NMR) spectra for hydrogen atoms were measured in the indicated solvent with tetramethylsilane (TMS) as the internal standard on a GE QE 300, a Bruker AC 300 or an IBM WP-100 spectrometer. The values are expressed in parts per million downfield from TMS. El and Cl mass spectra were obtained on a Finnigan MAT 8230 Double Focusing high resolution mass spectrometer. Sonications were carried out using a L+R model T 14-B 400 watt ultrasonic cleaner or a Branson DHA 1000 200 watt cleaner.

EXAMPLE 1

(E)-5-Carbethoxymethyliden-3-spirocyclopentyl-δ-valerolactone (a)

3,3-Tetramethyleneglutaric anhydride (5.9 g, 35 mmole) and carbethoxyethylidene triphenylphosphorane (12.2 g, 35 mmole) are dissolved in 350 mL of chloroform and refluxed for about 12 hours. The solvent is removed in vacuo and the yellow oil is chromatographed on silica gel eluting with hexane/40% ethyl acetate. 4.9 g, 59% of a water white oil was isolated and found to be the title compound.

$^1$H NMR (CDCl$_3$) 5.65 (1H, s); 4.18 (2H, q, J=7 Hz); 3.12 (2H, s); 2.6 (2H, s); 1.8–1.6 (4H, m); 1.6–1.5 (2H, m); 1.5–1.4 (2H, m); 1.3 (3H, t, J=7 Hz). Mass Spec. (DCI) m/z 239 (M+H). Analysis-calc'd for $C_{13}H_{18}O_4$: C, 65.53; H, 7.61; found: C, 65.08; H, 7.69.

EXAMPLE 2

(E)-5-Carbethoxymethylidene-3,3-dimethylvalerolactone (b)

The title compound is prepared as in Example 1 in a yield of 44% using 3,3-dimethylglutaric anhydride as the starting material. Mass Spec. (DCI) m/z 213 (M+H). Analysis-calc'd for $C_{11}H_{16}O_4$: C, 62.25; H, 7.60; found: C, 62.25; H, 7.55.

EXAMPLE 3

(E)-3-Carbethoxymethyliden-4,7-endoethylen-1-oxo-1,3,4,7 tetrahydroisobenzofuran (c)

The title compound is prepared as in Example 1 in a yield of 78% using endo-cis-bicyclo[2.2.2]oct-5-en-2,3-dicarboxylic anhydride as the starting material, mp 54°–55° C. Mass Spec. (DCI) m/z 249 (M+H). Analysis-calc'd for $C_{14}H_{16}O_4$: C, 67.72; H, 6.50; found: C, 67.51; H, 6.33.

EXAMPLE 4

(E)-3-Carbethoxymethyliden-4,7-endomethylen-1-oxo-1,3,4,7-tetrahydroisobenzofuran (d)

The title compound is prepared as in Example 1 in a yield of 70% using endo-cis-bicyclo[2.2.1]hept-5-en-2,3- dicarboxylic anhydride as the starting material. Mass Spec. (DCI) m/z 235 (M+H). Analysis-calc'd for $C_{13}H_{14}O_4$: C, 66.65; H, 6.02; found: C, 66.46; H, 5.98.

EXAMPLE 5

(E)-3-Carbethoxymethyliden-4,7-endopropylen-1-oxo-1,3,4,7-tetrahydroisobenzofuran (e)

The title compound is prepared as in Example 1 in a yield of 50% using endo-cis-bicyclo[3.2.2]non-5-en-2,3-dicarboxylic anhydride as the starting material. Mass Spec. (DCI) m/z 263 (M+H). Analysis-calc'd for $C_{15}H_{18}O_4$: C, 68.68; H, 6.92; found: C, 68.48; H, 6.92.

EXAMPLE 6

N-[4-(2-Carbomethoxyphenyl)benzyl]phthalimide (f)

Methyl 2-[4-(bromomethylene)phenyl]benzoate (1.22 g, 0.04 mole), phthalimide (0.59 g, 0.04 mole), and potassium carbonate (0.55 g, 0.04 mole) are combined in 120 mL acetonitrile. The mixture is heated at reflux for 24 hours. At that time the mixture is filtered through celite and rotovapped to a residue. The residue is crystallized from ethyl acetate to afford 1.1 g (71%) of the title compound as a tan solid mp 148°–150° C. $^1$H NMR (CDCl$_3$) 7.9–7.1 (12H, m); 4.92 (2H, s); 3.63 (3H, s). Mass Spec. (DCI) m/z 372 (M+H). Analysis -calc'd for $C_{23}H_{17}NO_4.\frac{1}{2} H_2O$: C, 72.62; H, 4.77: N, 3.68; found: C, 72.88; H, 4.55; N, 3.77.

EXAMPLE 7

N-[4-(2-Cyanophenyl)benzyl]phthalimide (g)

The title compound is prepared as in Example 6 in a yield of 76% using 4-(2-cyanophenyl)benzyl bromide as the starting material, mp 150°–153° C. Mass Spec. (DCI) m/z 339 (M+H). Analysis-calc'd for $C_{22}H_{14}N_2O_2.\frac{1}{4} H_2O$: C, 77.07; H, 4.26; N, 8.17; found: C, 77.12; H, 4.09; N, 8.47.

EXAMPLE 8

N-[4-(2-Tetrazolophenyl)benzyl]phthalimide (h)

Compound (g) of Example 7 (25.35 g, 0.075 mole), sodium azide (5.56 g, 0.083 mole) and tributyltinchloride (22.5 mL, 0.083 mole) are combined in 350 mL of xylenes and heated at reflux for 48 hours. The reaction is allowed to cool, rotovapped and the residue taken up in ethyl acetate. The ethyl acetate is washed with 10% HCl and a resulting precipitate is filtered. The supernatant is washed twice more with acid, once with brine, dried over sodium sulfate and rotovapped to an oil which is chromatographed on silica gel using ethyl acetate as the mobile phase. The resultant pure oil crystallized from ethyl acetate to afford a white crystalline solid, mp 220°–222° C. Mass Spec. (DCI) m/z 382 (M+H). Analysis-calc'd for $C_{22}H_{15}N_5O_2$: C, 69.30; H, 4.00; N, 18.40. found: C, 69.30; H, 3.92; N, 18.33.

EXAMPLE 9

4-(2-Carbomethoxyphenyl)benzylamine (i)

Compound (f) of Example 6 (3.85 g, 0.01 mole) is dissolved in 100 mL of absolute ethanol with warming. Hydrazine hydrate (7.5 mL) is added at once. The solution is heated to reflux for 10 minutes and the reaction mixture sets up. The mixture is cooled to room temperature and filtered. The precipitate is washed with excess hot ethanol. The ethanol fraction is rotovapped to a pale yellow oil. Chromatography on silica gel using methylene chloride/25% methanol as the mobile phase yields 1.6 g (66%) of a pale yellow oil. $^1$H NMR (CDCl$_3$) 7.83 (1H, d, J=7 Hz); 7.6–7.2 (7H, m); 3.92 (2H, s); 3.66 (3H, s); 2.16 (2H, bs). Mass Spec. (DCI) m/z 242 (M+H). Analysis-calc'd for $C_{15}H_{15}NO_2.H_2O$: C, 71.97; H, 6.44; N, 5.60; found: C, 71.60; H, 6.27; N, 5.70.

EXAMPLE 10

4-(2-Cyanophenyl)benzylamine (j)

The title compound is prepared as in Example 9 using compound (g) of Example 7 instead of compound (f) and used in further steps without purification. Mass Spec. (DCI) m/z 209 (M+H).

EXAMPLE 11

4-(2-Tetrazolophenyl)benzylamine (k)

The title compound is prepared as in Example 9 using compound (h) of Example 8 instead of compound (f) and used in further steps without purification. Mass Spec. (DCI) m/z 250 (M+H).

EXAMPLE 12

6-Carbethoxymethyliden-1-[4-(2-carbomethoxyphenyl)benzyl]-4,4-dimethylpiperidin-2-one (E & Z) mixture (I)

Compound (i) of Example 9 (1.2 g, 0.005 mole) and compound (b) of Example 2 (1.1 g, 0.005 mole) are combined in toluene (50 mL) and refluxed for 5 hours. The toluene is removed in vacuo and the residue is chromatographed on silica gel using hexane/ethyl acetate as the mobile phase. The title compound is isolated as a colorless oil (1.2 g, 52%). Mass Spec. (DCI) m/z 436 (M+H). Analysis-calc'd for $C_{26}H_{29}NO_5$: C, 70.96; H, 6.76; N, 3.18; found: C, 70.76; H, 7.11; N, 2.77.

EXAMPLE 13

3-Carbethoxymethyliden-2-[4-(2-carbomethoxyphenyl)benzyl]-4,7-endomethylen-1,3,4,7-tetrahydro-1-oxoisoindole (m)

The title compound is prepared as in Example 12 in a yield of 61% using compound (d) of Example 4 instead of compound (b). $^1$H NMR (CDCl$_3$) 7.82 (1H, d, J=7 Hz); 7.6–7.2 (7H, m); 6.15 (1H, m); 5.91 (1H, m); 5.05 (1H, s); 4.77 (1H, d, J=16 Hz); 4.45 (1H, d, J=16 Hz); 4.18 (2H, q, J=7 Hz); 4.10 (1H, m); 3.71 (1H, bs): 3.59 (3H, s); 3.40 (1H, bs); 3.22 (1H, m); 1.6 (2H, m); 1.26 (3H, t, J=7 Hz). See Table 1 for additional data.

TABLE 1

| | | Physical Data | | |
|---|---|---|---|---|
| Compound | Formula | MP °C. | Mass[1] Spec | Calc'd C, H, N Found C, H, N |
| m | $C_{28}H_{27}NO_5$ | foam | 458 | C, 72.78; H, 6.00; N, 3.03 |
| | | | | C, 72.51; H, 6.14; N, 2.89 |
| y | $C_{28}H_{29}NO_5$ | foam | 460 | C, 73.18; H, 6.36; N, 3.05 |

TABLE 1-continued

| Compound | Formula | Physical Data MP °C. | Mass[1] Spec | Calc'd C, H, N / Found C, H, N |
|---|---|---|---|---|
| n | $C_{29}H_{29}NO_5$ | 64–65 | 472 | C, 73.16; H, 6.69; N, 3.04 / C, 73.86; H, 6.20; N, 2.97 |
| o | $C_{29}H_{29}NO_5$ | 49–51 | 486 | C, 73.64; H, 6.21; N, 2.87 / C, 74.20; H, 6.43; N, 2.88 |
| p | $C_{28}H_{26}N_2O_3$ · monohydrate | 162–166 | 439 | C, 73.76; H, 6.41; N, 2.81 / C, 73.66; H, 6.18; N, 6.14 / C, 73.77; H, 6.24; N, 5.93 |
| q | $C_{27}H_{24}N_2O_3$ · 0.25 hydrate | 134–138 | 425 | C, 76.07; H, 5.72; N, 6.57 / C, 75.78; H, 5.61; N, 6.57 |
| w | $C_{29}H_{29}N_5O_4$ · $C_5H_5N$ · $1.5H_2O$ | 104–112 | 514 | C, 66.11; H, 6.04; N, 13.61 / C, 66.25; H, 5.67; N, 13.09 |
| z | $C_{27}H_{27}N_5O_3$ · 0.6 $CH_2Cl_2$ | 105–112 | 470 | C, 63.69; H, 5.46; N, 13.45 / C, 63.22; H, 5.33; N, 13.09 |
| aa | $C_{28}H_{29}N_5O_3$ · $C_5H_5N$ · 1.25 $CH_2Cl_2$ | 107–113 | 484 | C, 61.41; H, 5.64; N, 12.55 / C, 61.25; H, 5.65; N, 12.48 |
| r | $C_{28}H_{31}NO_5$ | 79–81 | 462 | C, 72.86; H, 6.77; N, 3.03 / C, 73.16; H, 6.61; N, 2.96 |
| t | $C_{27}H_{29}N_5O_3$ · $C_5H_5N$ | 80–90 | 472 | C, 69.80; H, 6.22; N, 15.26 / C, 70.10; H, 6.37; N, 15.02 |
| s | $C_{25}H_{27}N_5O_3$ · $C_5H_5N$ | 85–95 | 446 | C, 68.68; H, 6.15; N, 16.02 / C, 68.47; H, 6.36; N, 16.8 |
| x | $C_{24}H_{25}N_5O_3$ · $C_5H_5N$ · 0.5 $CH_2Cl_2$ | 58–65 | 432 | C, 64.07, H, 5.65; N, 15.20 / C, 64.11; H, 5.98; N, 14.85 |
| ab | $C_{25}H_{27}N_5O_3$ · $C_5H_5N$ · 0.5 $H_2O$ | 76–80 | 446 | C, 67.52; H, 6.23; N, 15.75 / C, 67.69; H, 6.68; N, 15.84 |
| ac | $C_{25}H_{29}N_5O_3$ · $C_5H_5N$ · 1.2 $H_2O$ | 80–88 | 472 | C, 67.16; H, 6.41; N, 14.69 / C, 67.57; H, 6.45; N, 14.24 |
| ad | $C_{28}H_{31}N_5O_3$ · $C_5H_5N$ · 1.3 $H_2O$ | 85–92 | 486 | C, 67.40; H, 6.62; N, 14.29 / C, 67.70; H, 6.58; N, 13.89 |
| ae | $C_{26}H_{29}N_5O_3$ · $C_5H_5N$ · 1.25 $H_2O$ | 79–84 | 460 | C, 66.35; H, 6.55; N, 14.97 / C, 66.16; H, 6.61; N, 14.70 |
| af | $C_{26}H_{27}N_5O_3$ · $C_5H_5N$ · 1.4 $H_2O$ | 98–106 | 458 | C, 66.27; H, 6.24; N, 14.96 / C, 66.56; H, 5.90; N, 14.48 |
| ag | $C_{29}H_{31}N_5O_3$; 2 $H_2O$ | 144–150 | 498 | C, 65.27; H, 6.61; N, 13.12 / C, 65.40; H, 6.18; N, 12.73 |
| ah | $C_{29}H_{29}N_5O_3$ · $C_5H_5N$ · 1.75 $H_2O$ | 120–127 | 496 | C, 67.37; H, 6.23; N, 13.86 / C, 67.79; H, 6.19, N, 13.37 |
| ai | $C_{26}H_{25}N_5O_4$ · $C_5H_5N$ 2.25 $H_2O$ | 115–125 | 472 | C, 62.98; H, 5.88; N, 14.21 / C, 62.75; H, 5.62; N, 13.81 |
| aj | $C_{40}H_{35}N_5O_3$ · $C_5H_5N$, EtOAc | 108–113 | 634 | C, 73.48; H, 6.04; N, 10.49 / C, 73.29; H, 5.78; N, 10.44 |
| ak | $C_{30}H_{31}N_5O_3$ · $C_5H_5N$ $H_2O$ | 223–226 | 510 | C, 69.29; H, 6.31; N, 13.85 / C, 69.32; H. 6.18; N, 13.70 |
| al | $C_{26}H_{30}N_5O_4$ $C_5H_5N$ · 1.5 $H_2O$, 0.5EtOAc | 58–68 | 478 | C, 63.14; H, 6.90; N, 13.39 / C, 63.28; H, 7.03; N, 13.50 |

[1] DCI spectrum gives (M + H) peak

EXAMPLE 14

3-Carbethoxymethyliden-2-[4-(2-carbomethoxyphenyl)benzyl]-4,7-endoethylen-1,3,4,7-tetrahydro-1-oxoisoindole (n)

The title compound is prepared as in Example 12 in a yield of 53% using compound (c) of Example 3 instead of compound (b). Data in Table 1.

EXAMPLE 15

3-Carbethoxymethyliden-2-[4-(2-carbomethoxyphenyl)benzyl]-4,7-endopropylen-1,3,4,7-tetrahydro-1-oxoisoindole (o)

The title compound is prepared as in Example 12 in a yield of 66% using compound (e) of Example 5 instead of compound (b). Data in Table 1.

EXAMPLE 16

3-Carbethoxymethyliden-2-[4-(2-cyanophenyl)benzyl]-4,7-endoethylen-1,3,4,7-tetrahydro-1-oxoisoindole (p)

The title compound is prepared as in Example 12 in a yield of 35% using compound (c) of Example 3 instead of compound (b), and compound (j) of Example 10 instead of compound (i). Data in Table 1.

EXAMPLE 17

3-Carbethoxymethyliden-2-[4-(2-cyanophenyl)benzyl]-4,7-endomethylen-1,3,4,7-tetrahydro-1-oxoisoindole (q)

The title compound is prepared as in Example 12 in a yield of 10% using compound (d) of Example 4 instead of compound (b), and compound (j) of Example 10 instead of compound (i). Data in Table 1.

EXAMPLE 18

6-Carbethoxymethyliden-1-[4-(2-carbomethoxyphenyl)benzyl]-4-spirocyclopentylpiperidin-2-one (r)

The title compound is prepared as in Example 12 in a yield of 45% using compound (a) of Example 1 instead of compound (b). Data in Table 1.

EXAMPLE 19

6-Carbethoxymethyliden-4,4-dimethyl-1-[4-(2-tetrazolophenyl)benzyl]piperidin-2-one Pyridinium salt (s)

Compound (k) of Example 11 (0.41 g, 0.0016 mole) and compound (b) of Example 2 (0.34 g, 0.0016 mole) are combined in pyridine (10 mL) containing 0.5 g molecular sieves (4 Å). The mixture is refluxed for 24 hours, cooled to room temperature and filtered. The solids are washed with ethyl acetate followed by methylene chloride. The combined filtrates are concentrated in vacuo and the residue is chromatographed on silica gel by eluting with hexane/70% ethyl acetate. The eluants are concentrated and crystallized from ethyl acetate to yield 335 mg (40%), mp 85°-95° C., of the title compound as a pale yellow solid. $^1$H NMR (CDCl$_3$) 7.85 (1H, d, J=7 Hz); 7.6–7.4 (3H, m); 7.30–7.05 (4H, m); 4.9–4.7 (2H, m); 4.7 (1H, s); 4.12 (2H, q, J=7 Hz); 2.3 (2H, s); 1.9 (2H, s); 1.26 (3H, s); 1.05 (6H, s). Mass Spec. (DCl) m/z 446 (M+H). Data in Table 1.

EXAMPLE 20

6-Carbethoxymethyliden-4-spirocyclopentyl-1-[4-(2-tetrazolophenyl)benzyl]piperidin-2-one Pyridinium Salt (t)

The title compound is prepared as in Example 19 in a yield of 80% using compound (a) of Example 1 instead of compound (b). Data in Table 1.

EXAMPLE 21

3-Carbethoxymethyliden-2-[4-(2-tetrazolophenyl)benzyl]-4,7-endoethylen-1,3,4,7-tetrahydro-1-oxoisoindole (u)

The title compound is prepared as in Example 19 using compound (c) of Example 3 instead of compound (b), and except that after the filtrates are concentrated, they are redissolved in methylene chloride, washed twice with 10% hydrochloric acid, dried over sodium sulfate, filtered, concentrated to a residue and then chromatographed as in Example 19. Yield 62%.

EXAMPLE 22

3-Carbethoxymethyliden-2-[4-(2-tetrazolophenyl)benzyl]-4,7-endomethylen-1,3,4,7-tetrahydro-1-oxoisoindole Pyridinium Salt (v)

The title compound is prepared as in Example 19 in a yield of 52%, mp 142°-145° C., using compound (d) of Example 4 instead of compound (b). Mass Spec. (DCl) m/z 468 (M+H). Analysis—calc'd for: C, 62.32; H, 4.91; N, 13.34; found: C, 62.54; H, 4.77; N, 13.14.

EXAMPLE 23

3-Carbomethoxymethyliden-2-[4-(2-tetrazolophenyl)-benzyl]-4-methoxy-4,7-endoethylen-1,3,4,7-tetrahydro-1-oxoisoindole Pyridinium Salt (w)

The title compound is prepared as in Example 19 in a yield of 66% using compound (c) of Example 3 instead of compound (b). Data in Table 1.

EXAMPLE 24

6-Carbethoxymethyliden-4-methyl-1-[4-(2-tetrazolophenyl)benzyl]piperidin-2-one Pyridinium Salt (x)

The title compound is prepared as in Example 19 in a yield of 51% using 5-carbethoxymethyliden-3-methylvalerolactone instead of compound (b). Data in Table 1.

EXAMPLE 25

3-Carbethoxymethyliden-2-[4-(2-carbomethoxyphenyl)benzyl]-4,7-endomethylen-1,3,4,5,6,7-hexahydro-1-oxoisoindole (y)

Compound (m) of Example 13 (0.46 g, 0.001 mole), cyclohexene (1.6 g, 0.02 mole), and 10% Pd.C (250 mg) are refluxed in 50 mL 100% ethanol for 3 hours. The mixture is filtered through celite and concentrated in vacuo. The white foam is chromatographed on silica gel using hexane/15% ethyl acetate as the mobile phase to yield 0.43 g (92%) of the title compound as a white foam.

$^1$H NMR (CDCl$_3$) shows the loss of the vinyl protons at 6.15 and 5.91. Data in Table 1.

EXAMPLE 26

3-Carbethoxymethyliden-2-[4-2-(tetrazolophenyl)benzyl]-4,7-endomethylen-1,3,4,5,6,7-hexahydro-1-oxoisoindole (z)

The title compound is prepared as in Example 25 in a yield of 91% using compound (v) of Example 22 instead of compound (m). Data in Table 1.

EXAMPLE 27

3-Carbethoxymethyliden-2-[4-(2-tetrazolophenyl)benzyl]-4,7-endomethylen-1,3,4,5,6,7-hexahydro-1-oxoisoindole Pyridinium salt (aa)

The title compound is prepared as in Example 25 in a yield of 88% using compound (u) of Example 21 instead of compound (m). Data in Table 1.

EXAMPLE 28

6-Carbethoxymethylidene-5,5-dimethyl-1-[4-(2-tetrazolophenyl)benzyl]piperidin-2-one Pyridinium Salt (ab)

The title compound is prepared as in Example 19 in a yield of 82%, using 5-carbethoxymethyliden-4,4-dimethylvalerolactone instead of compound (b). Data in Table 1.

EXAMPLE 29

5-Carbethoxymethyliden-4-spirocyclohexyl-1-[4-(2-tetrazolophenyl)benzyl]pyrrolidin-2-one Pyridinium Salt, 1.2 Hydrate (ac)

The title compound is prepared as in Example 19 in a yield of 81%, using 4-carbethoxymethyliden-3-spirocyclohexylbutyrolactone instead of compound (b). Data in Table 1.

EXAMPLE 30

5-Carbethoxymethylidine-4-spirocycloheptyl-1-[4-(2-tetrazolophenyl)benzyl]pyrrolidin-2-one Pyridinium Salt, 1.3 Hydrate (ad)

The title compound is prepared as in Example 19 in a yield of 67%, using 4-carbethoxymethyliden-3-spirocycloheptyllbutyrolactone instead of compound (b). Data in Table 1.

EXAMPLE 31

6-Carbethoxymethyliden-4-ethyl-4-methyl-1-[4-(2-tetrazolophenyl)benzyl]piperidine-2-one Pyridinium Salt, 1.25 Hydrate (ae)

The title compound is prepared as in Example 19 in a yield of 51%, using 5-carbethoxymethyliden-3-ethyl-3-methyl-δ-valerolactone instead of compound (b). Data in Table 1.

EXAMPLE 32

5-Carbethoxymethylidine-4-spirocyclopentyl-1-[4-(2-tetrazolophenyl)benzyl]pyrrolidin-5-one Pyridinium Salt, 1.4 Hydrate (af)

The title compound is prepared as in Example 19 in a yield of 18%, using 4-carbethoxymethyliden-3-spirocyclopentylbutyrolactone instead of compound (b). Data in Table 1.

EXAMPLE 33

3-Carbethoxymethyliden-2-[4-(2-tetrazolophenyl)benzyl]-4,7-endopropylen-1,3,4,5,6,7-hexahydro-1-oxoisoindole Dihydrate (ag)

The title compound is prepared as in Example 25 in a yield of 44%, using compound (ah) of Example 46 instead of compound (b). Data in Table 1.

EXAMPLE 34

3-Carbethoxymethyliden-2-[4-(2-tetrazolophenyl)benzyl]-4,7-endopropylen-1,3,4,7-tetrahydro-1-oxoisoindole Pyridinium Salt, 1.75 Hydrate (ah)

The title compound is prepared as in Example 19 in a yield of 60%, using compound (e) of Example 5 instead of compound (b). Data in Table 1.

EXAMPLE 35

3-Carbethoxymethyliden-2-[4-(2-tetrazolophenyl)benzyl]-4,7-endoxohexahydro-1-oxoisoindole Pyridinium Salt, 2.25 Hydrate (ai)

The title compound is prepared as in Example 19 in a yield of 36%, using 3-carbethoxymethyliden-4,7-endohexahydroisobenzofuran instead of compound (b). Data in Table 1.

EXAMPLE 36

3-Carbethoxymethyliden-2-[4-(2-tetrazolophenyl)benzyl]-4,7-(diphenylmethylidino)endomethylenehexahydro-1-oxoisoindole Pyridinium Salt, EtOAc solvate (aj)

The title compound is prepared as in Example 19 in a yield of 28%, using 3-carbethoxymethyliden-4,7-(diphenylmethylidino)endomethylenehexahydro-1-oxoisobenzofuran instead of compound (b). Data in Table 1.

EXAMPLE 37

3-Carbethoxymethyliden-2-[4-(2-tetrazolophenyl)benzyl]-4,7-(dimethylmethylidino)endomethylenehexahydro-1-oxoisoindole Pyridinium Salt Monohydrate (ak)

The title compound is prepared as in Example 19 in a yield of 43%, using 3-carbethoxymethyliden-4,7-(dimethylmethylidino)endomethylenehexahydro-1-oxoisobenzofuran instead of compound (b). Data in Table 1.

EXAMPLE 38

6-Carbethoxymethylen-6-hydroxy-4-ethyl-4-methyl-1-[4-(2-tetrazolophenyl)benzyl]piperidin-2-one Pyridinium salt.1.5 H$_2$O.0.5 EtOAc (al).

5-Carbethoxymethyliden-3-ethyl-3-methyl-(delta)-valerolactone (10 g, 49 mmole) and compound (k) (8.1 g, 32 mmole) are combined in pyridine (100 mL) and 4 Å molecular sieves (100 mg) were added. The reaction mixture is warmed to 50° C. for 16 hours. The reaction is then cooled and the pyridine removed in vacuo to yield a residue. The residue is extracted with methylene chloride (300 mL) and filtered. The precipitate is washed with an additional 100 mL of methylene chloride. The combined extracts are concentrated in vacuo and chromatographed on silica gel using first hexane/40% EtOAc then hexane/60% EtOAc as the mobile phases. Removal of the solvent and vacuum drying yields 7.34 g (51%) of the title compound. $^1$H NMR (CDCl$_3$) shows the two, CH$_2$CO$_2$Et protons as a singlet at 3.44.

EXAMPLE 39

2-(4-Aminomethylbenzyl)benzoic acid (am)

Methyl 2-(4-aminomethylbenzyl)benzoate (2.41 g, 0.01 moles) is dissolved in 50 mL methanol and 10 mL of 50% KOH is added. The mixture is heated at reflux for 6 hours, concentrated in vacuo and then acidified to yield 1.3 g (57%) of title compound as a precipitate. Mass Spec (DCI) m/z 228. Further purification is achieved by forming the HCl salt in isopropanol/saturated with HCl gas.

EXAMPLE 40

Inhibition of Angiotensin II Dose-Response in Rabbit Thoracic Aorta

Purpose: To identify competitive receptor antagonists of an angiotensin II-1 activity, i.e., angiotensin II-induced vasoconstriction in in vitro aortic rings. [Chiu, A. T., McCall, D. E., Price, W. A., Wong, P. C., Carini, D. J., Duncia, J. V., Wexler, R. R., Yoo, S. E., Johnson, A. L., and Timmermans, P.B.M.W.M.: Nonpeptide angiotensin II receptor antagonists. VII. Cellular and Biochemical pharmacology of DuP 753, an orally active antihypertensive agent. *J. Pharmacol, Exp. Ther.*, 252, 726 (1990)]

Solution Preparation: Angiotensin II acetate (Sigma, A-9525) is diluted to a concentration of 0.5 mg/mL in deionized distilled water and frozen in 0.25 mL aliquots. For each test an aliquot is freshly thawed and serially diluted with Krebs bicarbonate buffer to provide stock solutions of angiotensin II in buffer for addition to the tissue baths. Stock solutions are made such that cumulative additions of angiotensin II stock to each bath provide final bath concentrations of $3 \times 10^{-10}$, $1 \times 10^{-9}$, $3 \times 10^{-9}$, $1 \times 10^{-8}$, $3 \times 10^{-8}$, and $1 \times 10^{-7}$M angiotensin II, in order to evaluate graded dose-response of the tissue to angiotensin II. Test compounds are diluted in dimethylsulfoxide vehicle such that a 50 μL addition to the tissue bath produces a final bath concentration of $1 \times 10^{-5}$M compound in Krebs-bicarbonate buffer (baths contain 15 mL Krebs-bicarbonate buffer).

Procedure: 1.8 to 2.3 kg New Zealand white rabbits are sacrificed with an intravenous sodium pentobarbital overdose and the thoracic aorta gently dissected free from the aortic root to the level of the diaphragm, into ice cold Krebs bicarbonate buffer. The aorta is gently freed of clots and adventitia and cleanly cut into 5 mm segments. Each ring is suspended from a Gould isotonic force transducer in a tissue bath containing 15 mL oxygenated Krebs bicarbonate buffer regulated at 37° C. Initial tension is adjusted to 4.0 g and equilibrated over three 20-minute wash periods with fresh Krebs-bicarbonate buffer to achieve a baseline tension of 3.0 g. Graded angiotensin II doses are given cumulatively to achieve a maximal contraction. Three 20-minute Krebs-bicarbonate buffer washes are performed to remove the initial angiotensin II effect. The test compound is then given at a screening concentration of $1.0 \times 10^{-5}$ μM. After observing any effects of the test compound along, the angiotensin II cumulative dose-response is then repeated in the presence of the test compound. In addition, since the test compounds are dissolved in DMSO, DMSO alone is tested in two rings as a vehicle control in each screening experiment. In this assay, vehicle alone shows a percent inhibition of $5.2 \pm 0.7\%$ (n=23 tests).

Analysis: Angiotensin II vasoconstrictor tension in grams is expressed as a percent of maximal contraction for the before and after test compound angiotensin II dose-responses. Angiotensin II $ED_{50}$ and $ED_{90}$ is determined from the angiotensin II dose-response curves generated before and after test compound. Mean $ED_{50}$ values for angiotensin II before and after DMSO vehicle treatment are $1.02 \times 10^{-9}$ ($9.30 \times 10^{-10} - 1.11 \times 10^{-9}$, 95% C.L.) and $1.88 \times 10^{-9}$ ($1.71 \times 10^{-9} - 2.05 \times 10^{-9}$, 95% C.L.) M, respectively. Mean $ED_{90}$ values for angiotensin II before and after DMSO vehicle treatment are $4.44 \times 10^{-9}$ ($4.21 \times 10^{-9} - 4.67 \times 10^{-9}$, 95% C.L.) and $5.88 \times 10^{-9}$ ($5.57 \times 10^{-9} - 6.20 \times 10^{-9}$, 95% C.L.) M, respectively. A percent inhibition of the angiotensin II dose-response is calculated by determining the percent of maximal contraction occurring after the test compound at the concentration that achieved a 90% contraction before antagonist: 90% contraction occurring after test compound at the $ED_{90}$ before test compound/$90 \times 100 = \%$ Inhibition. See Table 2 for results.

EXAMPLE 41

Angiotensin II Antagonist Dose-Response in Rabbit Thoracic Aorta

Purpose: To assess potency of competitive receptor antagonists of an angiotensin II-1 activity, i.e., angiotensin II-induced vasoconstriction in vitro aortic rings. [Chiu, A. T., McCall, D. E., Price, W. A., Wong, P. C., Carini, D. J., Dunica, J. V., Wexler, R. R., Yoo, S. E., Johnson, A. L., and Timmermans, P. B. M. W. M.: Nonpeptide angiotensin II receptor antagonists. VII. Cellular and Biochemical pharmacology of DuP 753, an orally active antihypertensive agent. *J. Pharmacol. Exp. Ther.*, 252, 726 (1990)].

Solution Preparation: Angiotensin II acetate (Sigma, A-9525) is diluted to a concentration of 0.5 mg/mL in deionized distilled water and frozen in 0.25 mL aliquots. For each test an aliquot is freshly thawed and serially diluted with Krebs bicarbonate buffer to provide stock solutions of angiotensin II in buffer for addition to the tissue baths. Stock solutions are made such that cumulative additions of angiotensin II stock to each bath provide final bath concentrations of $3 \times 10^{-10}$, $1 \times 10^{-9}$, $3 \times 10^{-9}$, $1 \times 10^{-8}$, $3 \times 10^{-8}$, and $1 \times 10^{-7}$M angiotensin II, in order to evaluate graded dose-response of the tissue to angiotensin II. Test compounds are serially diluted in dimethylsulfoxide vehicle such that a 50 μL addition to the tissue bath produces a final bath concentration of from $1 \times 10^{-7}$ to $1 \times 10^{-9}$M compound in Krebs-bicarbonate buffer (baths contain 15 mL Krebs-bicarbonate buffer), in order to assess dose-response characteristics of the compound's inhibition of angiotensin II contractile activity.

Procedure: 1.8 to 2.3 kg New Zealand white rabbits are sacrificed with an intravenous sodium pentobarbital overdose and the thoracic aorta gently dissected free from the aortic root to the level of the diaphragm, into ice cold Krebs bicarbonate buffer. The aorta is gently freed of clots and adventitia and cleanly cut into 5 mm segments. Each ring is suspended from a Gould isotonic force transducer in a tissue bath containing 15 mL oxygenated Krebs bicarbonate buffer regulated at 37° C. Initial tension is adjusted to 4.0 g and equilibrated over three 20-minute wash periods with fresh Krebs-bicarbonate buffer to achieve a baseline tension of 3.0 g. Graded angiotensin II doses are given cumulatively to achieve a maximal contraction. Three 20-minute washes with fresh Krebs-bicarbonate buffer are performed to remove the initial angiotensin II effect. The test compound is then given to separate rings at different antagonist concentrations (n=2 rings/test concentration) in order to asses antagonist dose-response. The angiotensin II cumulative dose-response is then repeated in the presence of the test compound.

Analysis: Angiotensin II vasoconstrictor tension in grams is expressed as a percent of maximal contraction for the before and after test compound angiotensin II dose-responses. Angiotensin II $ED_{50}$ is determined from the angiotensin II dose-response curves generated before and after test compound. A Schild plot is constructed by plotting log (angiotensin II $ED_{50}$ after antagonist/$ED_{50}$ before antagonist-1) vs. -log(antagonist concentration). A pA2 is calculated from the Schild plot regression line at y=0. See results in Table 2.

EXAMPLE 42

Test Procedure for Screening Potential Angiotensin Receptor Antagonists in Salt-Depleted Normotensive Rats Purpose: This test is designed to detect hypotensive effects of a compound after oral dosing in normotensive animals made renin-dependent by salt depletion. [Wong, P. C., Price, W. A., Chiu, A. T., Duncia, J. V., Carini, D. J., Wexler, R. R., Johnson, A. L., and Timmermans, P. B. M. W. M.: Nonpeptide angiotensin II receptor antagonists. VIII. Characterization of functional antagonism displayed by DuP 753, an orally active antihypertensive agent. *J. Pharmacol. Exp. Ther.*, 252, 726 (1990)].

Solution Preparation: Oral 50 mg/kg furosemide doses are prepared from 10 mg/mL solutions of the intravenous pharmaceutical preparation (Lasix injection, Hoechst-Roussel Pharmaceutical). Test compound is uniformly suspended in 1% methylcellulose.

Method: Male 350–450 g Sprague-Dawley rats are implanted with teflon microcannulae via the middle caudal artery under 20 mg/kg intravenous brevital anesthesia and permitted a 4–7 day surgical recovery period. Throughout recovery and testing animals are individually housed unrestrained in standard rat metabolism cages and receive continuous 0.5 mL/hour intra-arterial 0.25N saline infusion through a spring-shielded swivelling tether connected to an infusion/blood pressure recording system to maintain arterial cannula patency. Animals are maintained on Low Sodium (0.03%) Purina Rat Chow #5881 throughout the study. After the recovery period animals are given oral 50 mg/kg furosemide (Lasix, Hoechst-Roussel Pharmaceutical) doses on two consecutive days to produce marked diuresis and plasma volume depletion that makes maintenance of normal blood pressure highly dependent on function of the renin-angiotensin-aldosterone system. Three hours after the second furosemide dose, rats are given test compound uniformly suspended in 1% methylcellulose (n=3/dose level) or 1 mL 1% methylcellulose vehicle (n=3) orally by gavage and blood pressure is continuously recorded for 24 h using a Buxco computerized data recording system. Compound-induced changes in blood pressure are compared to concurrent vehicle control blood pressures in order to detect drug effect.

Interpretation: Prior to salt depletion, normotensive rats typically show a plasma renin activity (PRA), measured by Radioimmuno Assay (RIA) of Angiotensin I (as ng Angiotensin I/mL plasma/hour) and yields a RIA of 0.7. After the salt-depletion protocol PRA values taken 3 hour after the furosemide dose have risen to about 7.4. Whereas blood pressure of normotensive rats that have not been salt-depleted does not change in response to treatment with the nonpeptide angiotensin receptor antagonist, DuP-753, salt-depleted animals typically respond with a blood pressure decrease of about 35 mmHg (mean arterial pressure, MAP). PRA is increased by this DuP-753 treatment to about 41.4.

Compounds that decrease blood pressure 10 or more mmHg (MAP) compared to concurrent control after oral dosing are considered active in this test. Maximum possible response is about $-35$ mmHg. See results in Table 2.

TABLE 2

| Compound | Biological Activity | | |
|---|---|---|---|
| | % Inh @ $10^{-5}$M | pA2 | Antihypertensive Activity (p.o.) |
| ah | 100 | 7.85 | active @ > 30 mpk |
| m | 0 | — | " |
| y | 0 | — | " |
| p | 3 | — | " |
| q | 10 | — | " |
| u | 99 | 8.16 | active @ 30 mpk |
| t | 100 | 7.85 | active @ 30 mpk |
| s | 100 | 7.40 | active @ 30 mpk |
| v | 100 | 8.35 | |
| z | 100 | 8.98 | active @ 30 mpk |
| aa | 100 | | active @ 30 mpk |
| ag | 100 | | active @ 30 mpk |
| ae | 100 | 8.97 | active @ 10 mpk |
| af | 100 | 8.44 | active @ 30 mpk |
| ac | 100 | 7.93 | active @ 30 mpk |
| ad | 100 | 8.36 | active @ 30 mpk |

What is claimed is:

1. A compound of the following formula

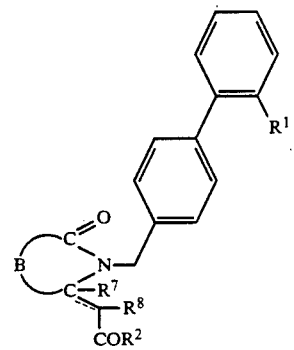

wherein B is a bisfused radical of the following formula

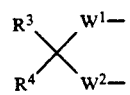

$W^1$ is $(CH_2)m$;
m is 0, 1, 2
$W^2$ is $(CH_2)n$;
n is 0, 1, 2
$R^1$ is $C_{1-4}$ alkoxycarbonyl or tetrozolo;
$R^2$ is hydroxy, $C_{1-4}$ alkoxy, $(C_{1-6}$ alkyl)HN, di($C_{1-6}$ alkyl)N, (HO)HN, (HO)($C_{1-6}$ alkyl)N, $(C_{1-4}$ alkoxy)($C_{1-6}$ alkyl)N, phenoxy or substituted phenoxy;
$R^3$ and $R^4$ are each independently hydrogen, $C_{1-6}$ alkyl, $C_{3-8}$ cycloalkyl, aryl, or $R^3$ and $R^4$ taken together form a $C_{3-8}$ carbocyclic ring;
$R^7$ is hydrogen or hydroxy;
$R^8$ is hydrogen;
$R^7$ and $R^8$ taken together form a bond;
the===bond is a single or a double bond; and pharmaceutically acceptable salts thereof; with the proviso that $R^7$ and $R^8$ taken together form a bond, $R^7$ and $R^8$ are hydrogen or $R^7$ is hydroxy and $R^8$ is hydrogen, then the bond is a single bond where $R^7$ and $R^8$ are hydrogen or $R^7$ is hydroxy and $R^8$ is hydrogen then the bond is a single bond.

2. The compound of claim 1 wherein $R^1$ is $C_{1-4}$ alkoxycarbonyl or tetrazolo.

3. The compound of claim 2 wherein $R^1$ is tetrazolo.

4. The compound of claim 1 wherein $R^7$ and $R^8$ taken together form a bond.

5. The compound of claim 1 which is an individual E or Z stereoisomer.

6. The compound of claim 1 selected from the group consisting of 6-carbethoxymethyliden-4-spirocyclopentyl-1-[4-(2-tetrazolophenyl)benzyl]piperidin-2-one pyridinium salt; 6-carbethoxymethyliden-4-ethyl-4-methyl-1-[4-(2-tetrazolophenyl)benzyl]piperdin-2-one pyridinium salt; 6-carbethoxymethyliden-4,4-dimethyl-1-[4-(2-tetrazolophenyl)benzyl]piperidin-2-one pyridinium salt and 6-carbethoxymethylen-4-ethyl-6-hydroxy-4-methyl-1-[4-(2-tetrazolophenyl)benzyl]piperidin-2-one pyridinium salt.

7. The compound of claim 1 which is 6-carbethoxymethyliden-4-spirocyclopentyl-1-[4-(2-tetrazolophenyl)benzyl]piperidin-2-one pyridinium salt.

8. The compound of claim 1 which is 6-carbethoxymethyliden-4-ethyl-4-methyl-1-[4-(2-tetrazolophenyl)benzyl]piperdin-2-one pyridinium salt.

9. A pharmaceutical composition comprising an effective amount of a compound of claim 1 as the active ingredient dispersed in a pharmaceutically acceptable carrier.

10. A method of treating a physiological condition in a mammal that is mediated by angiotensin II which comprises administering to the mammal an effective amount of the angiotensin II receptor antagonist compound of claim 1.

* * * * *